United States Patent [19]

Cale, Jr.

[11] 4,242,261
[45] Dec. 30, 1980

[54] PRODUCTION OF METHYLENE-CYCLOAMINES

[75] Inventor: Albert D. Cale, Jr., Mechanicsville, Va.

[73] Assignee: A. H. Robins Company, Inc., Richmond, Va.

[21] Appl. No.: 59,092

[22] Filed: Jul. 19, 1979

[51] Int. Cl.³ .................. C07D 205/06; C07D 211/70; C07D 207/20; C07D 223/04
[52] U.S. Cl. .......................... 260/239 A; 260/239 B; 260/326.8; 260/326.87; 260/326.2; 546/192; 546/230; 546/232; 260/326.47; 260/326.62
[58] Field of Search ......... 260/239 AR, 239 B, 326.8, 260/326.87; 546/192

[56] References Cited
U.S. PATENT DOCUMENTS 4,133,881   1/1979   Cale, Jr. et al. ............... 260/239 A

*Primary Examiner*—Mark L. Berch

[57] ABSTRACT

This invention provides an improved process for producing methylene-cycloamines as exemplified by 1-isopropyl-3-diphenylmethyleneacetidine:

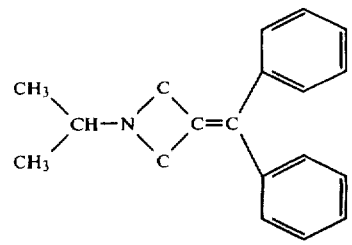

In accordance with the invention process, the above illustrated methyleneazetidine compound is synthesized by (1) reacting α,α-diphenyl-α-(1-isopropyl-3-azetidinyl) acetamide with bromine and alkali metal alkoxide under modified Hofmann Rearrangement conditions to form a carbamate intermediate, and (2) heating the carbamate intermediate in an acidic medium to yield the 1-isopropyl-3-diphenylmethyleneazetidine product.

This illustrated 3-methyleneazetidine compound is characterized by a combination of pharmacological properties which are indicative of utility as a mood elevating therapeutic agent for relieving the symptoms of depression in humans.

15 Claims, No Drawings

PRODUCTION OF METHYLENE-CYCLOAMINES

BACKGROUND OF THE INVENTION

Prior art technology of general interest in connection with the present invention are the procedures for producing compounds such as α-(1-R-3-pyrrolidinyl)-α,α-diphenylacetamides (and -acetonitriles) and α-(1-R-3-pyrrolidinyl)-α-phenyl-α-(2-pyridyl)acetamides (and -acetonitriles) which are disclosed in U.S. Pat. Nos. 3,192,206; 3,192,210; 3,192,221; 3,102,230; and 4,002,766.

Also of interest are the synthesis methods for producing antidepressant 3-disubstituted methylenepyrrolidines which are described in U.S. Pat. No. 3,732,247. The methylenepyrrolidines of the patent correspond to the formula:

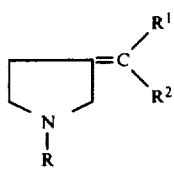

wherein R is selected from the group consisting of hydrogen, lower-alkyl, phenyl-lower-alkyl, substituted phenyl-lower-alkyl, cycloalkyl, phenoxy-lower-alkyl, phenylamino-lower-alkyl, and substituted phenyl, said lower-alkyl being limited to contain 2 to 8 carbon atoms when $R^1$ and $R^2$ are both phenyl; $R^1$ is selected from the group consisting of lower-alkyl, phenyl-lower-alkyl, cycloalkyl, phenyl and substituted phenyl; and $R^2$ is selected from the group consisting of phenyl and substituted phenyl.

U.S. Pat. No. 4,133,881 describes the production of a class of α-(1-R-3-azetidinyl)-α-phenyl-α-substituted-acetamides and -acetonitriles corresponding to the following formula:

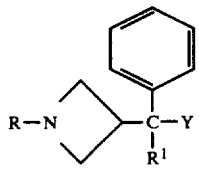

wherein R represents hydrogen, lower alkyl, lower cycloalkyl or phenyl-lower-alkyl, $R^1$ represents phenyl or 2-pyridyl, and Y is carbamoyl or cyano, which compounds exhibit antiarrhythmic activity.

Accordingly, it is a main object of the present invention to provide an improved process for producing methylene-cycloamine compounds such as 3-methyleneazetidine compounds which are characterized by one or more pharmacological properties useful for counteracting specific physiological abnormalities in humans and other mammals.

It is another object of this invention to provide a new and efficient method for converting a compound such as α,α-diphenyl-α-(1-ethyl-3-pyrrolidinyl)acetamide to a methylenecycloamine compound such as 1-ethyl-3-diphenylmethylenepyrrolidine.

Other objects and advantages shall become apparent from the accompanying description and examples.

DESCRIPTION OF THE INVENTION

One or more objects of the present invention are accomplished by the provision of a process for producing methylene-cycloamines which involves reacting a substituted acetamide compound described more fully hereinafter, under modified Hofmann Reaction conditions in the presence of alkanol to form a carbamate intermediate, and thereafter heating the said carbamate intermediate in an acidic medium to yield methylene-cycloamine product. Rather than the normal expected hydrolysis of a carbamate to an amine, the elimination of the equivalent of an alkylcarbamate molecule occurs forming a double bond.

In one embodiment, this invention provides a process for producing pharmacologically active methylene-cycloamine compounds which comprises (1) reacting a substituted acetamide compound with bromine and alkali metal alkoxide to produce a carbamate intermediate, wherein said substituted acetamide starting material corresponds to the formula:

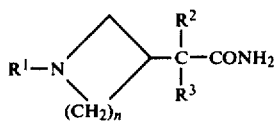

where $R^1$ is selected from lower alkyl, phenyl-lower-alkyl and cycloalkyl radicals, $R^2$ and $R^3$ are selected from phenyl and lower-alkylphenyl radicals, and n is an integer between 1 and about 4; and (2) heating said carbamate intermediate in an acidic medium to yield a methylene-cycloamine product corresponding to the formula:

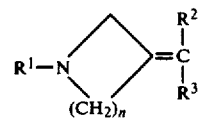

where $R^1$, $R^2$, $R^3$ and n are as previously defined. $R^2$ and $R^3$ can be the same or different.

By "lower-alkyl" is meant alkyl radicals having 1 to 8 carbon atoms. By "cycloalkyl" is meant cycloalkyl radicals having 1 to 9 carbon atoms.

Illustrative of $R^1$ radicals as represented in Formula I above are methyl, ethyl, isopropyl, butyl, isobutyl, hexyl, octyl, cyclopropyl, cyclopentyl, cycloheptyl, phenylethyl, α-methylbenzyl, phenylpropyl, and other equivalent lower alkyl, phenyl-lower-alkyl and cycloalkyl radicals.

Illustrative of $R^2$ and $R^3$ radicals are phenyl, 4-methylphenyl, 2-ethylphenyl, 4-isopropylphenyl, and the like.

Preparation of Substituted Cycloamino-Acetamide Starting Material

The cycloamino-acetamide compounds employed as starting material in the present invention process can be conveniently prepared by a synthesis procedure which is illustrated by the following reaction sequence:

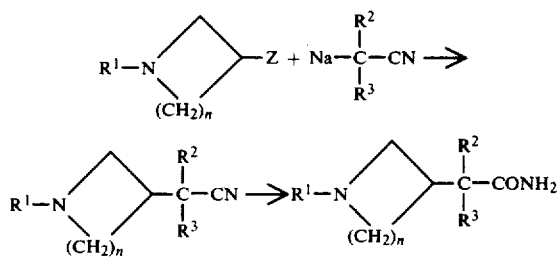

where $R^1$, $R^2$, $R^3$ and n are as previously defined and Z is —$OSO_2CH_3$(mesyloxy) or halide.

The preparation of 1-substituted-3-azetidinols and other 1,3-disubstituted azetidine derivatives are described in Tetrahedron Letters, No. 39, 4691 (1966); Tetrahedron Letters, No. 23, 2155 (1967); J. Org. Chem., 32, 2972 (1967); Chem. Pharm. Bull. 22, 1490 (1974); and German Offen. No. 1.932.219.

In the above illustrated reaction sequence flow diagram, the disubstituted acetonitrile (e.g., α,α-diphenylacetonitrile) is first metalated in a dry aprotic solvent employing sodium hydride or sodamide to provide sodio α,α-diphenylacetonitrile, which is reacted with a selected 1-R-3-mesyloxyazetidine or a 1-R-3-haloazetidine to yield an α-(1-R-3-zaetidinyl)-α,α-diphenylacetonitrile. The said acetonitrile derivative is then acid-hydrolyzed to α-(1-R-3-azetidinyl)-α,α-diphenylacetamide, which is a key starting material for the novel method of preparing methylene-cycloamine compounds in accordance with the present invention.

First Step of Invention Process

The first step of the invention process involves reacting the substituted acetamide starting material [e.g., the α-(1-R-3-azetidinyl)-α,α-diphenylacetamide described above] with bromine and an alkoxide ion in the presence of alkanol to form a carbamate intermediate. The following reaction sequence illustrates the first step of the process employing bromine and sodium methoxide in methanolic solution:

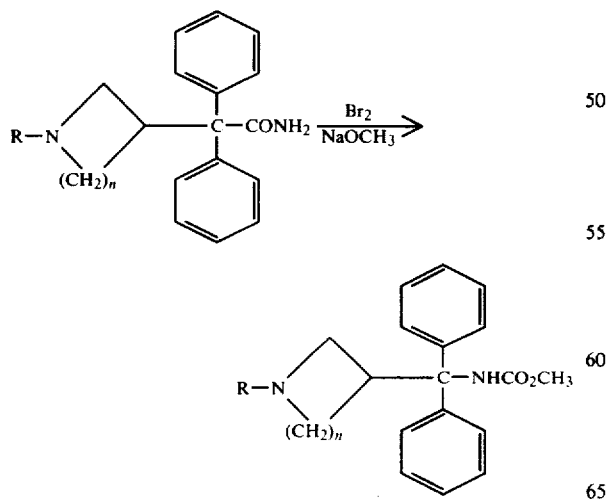

The said reaction sequence essentially corresponds to a modified Hofmann Rearrangement synthesis procedure for converting an amide to a carbamate derivative via a bromamide intermediate:

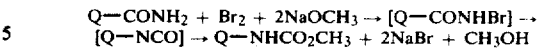

Q—$CONH_2$ + $Br_2$ + 2$NaOCH_3$ → [Q—CONHBr] → [Q—NCO] → Q—$NHCO_2CH_3$ + 2NaBr + $CH_3OH$

The alkali metal alkoxide employed is preferably a sodium or potassium alcoholate of an alkanol containing between one and about eight carbon atoms, e.g., methanol, ethanol, butanol, hexanol, octanol, and the like.

For purposes of efficiency, it is preferred to employ the alkali metal alkoxide and bromide in at least stoichiometric quantities with respect to the quantity of substituted acetamide starting material. For example, for each mole of substituted acetamide there can be employed between about 1 and 1.5 moles of bromine, and between about 2 and 2.5 moles of alkali metal alkoxide.

The reaction medium for the substituted acetamide conversion to carbamate derivative can be any anhydrous solvent which has acceptable solubility characteristics and which is stable under Hofmann Reaction conditions. Illustrative of suitable solvents are alcohols, ketones, ethers, hydrocarbons, halocarbons, and the like. It is particularly advantageous to employ methanol as a reaction medium in combination with bromine and alkali metal methoxide.

The substituted acetamide conversion step of the invention process is conducted at a temperature in the range between about −10° C. and 75° C. and preferably at a temperature in the range between about 0° C. and 50° C.

A more complete description of the variations and modifications of Hofmann Reaction conditions is presented in Organic Reactions, 3, 267 (John Wiley & Sons, New York, 1946); Survey of Organic Synthesis, Buehler and Pearson, (Wiley-Interscience, New York, 1970); and Chem. Ber., 87, 1294 (1954).

Second Step of the Invention Process

The carbamate intermediate produced in the first step of the invention process corresponds to the formula:

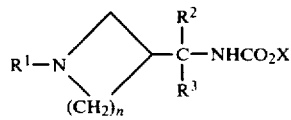

wherein $R^1$, $R^2$, $R^3$ and n are as previously defined, and X is an alkyl radical containing between one and about eight carbon atoms.

In the second step of the invention process, the carbamate intermediate is heated in an acidic medium preferably at a temperature between about 75° C. and 200° C., to yield a methylene-cycloamine product corresponding to the formula:

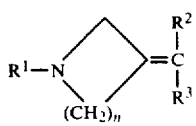

where $R^1$, $R^2$, $R^3$ and n are as previously defined.

The acidic medium normally will be an aqueous acid solution, or an acidic aqueous mixture of a water-miscible solvent such as tetrahydrofuran. If desired, the second step can be conducted in a reaction medium of an organic phase and an aqueous phase with suitable stirring means for efficient contacting of the phases.

The acidity of the reaction medium is adjusted with an inorganic acid so as to maintain at least a normality of 1 during the heating phase. The acidity preferably is provided by the use of sulfuric acid, preferably at about 6 to 18 normality. Illustrative of other suitable acids are hydrochloric acid and phosphoric acid, and the like.

The heating phase of the second step of the invention process is conducted for a period of time sufficient to complete the conversion of carbamate intermediate to methylene-cycloamine product. A typical reaction time will vary in the range between about 1 hour and 20 hours, depending on the acid strength and the temperature of the reaction medium. The reaction temperature during the heating phase can be varied in the range between about 50° C. and 250° C., and is preferably maintained in the range between about 75° C. and 200° C.

At the completion of the heating phase, the methylene-cycloamine product can be recovered by conventional extraction and distillation means. In a typical product recovery procedure, the reaction product medium is neutralized with a basic reagent, and the methylene-cycloamine product is extracted with a water-immiscible solvent such as benzene or ethyl acetate, and the final product is isolated by fractional distillation.

Pharmacology of the Methylene-cycloamine Products of the Invention Process

As previously described hereinabove, the present invention process is applicable for the production of pharmacologically active methylene-cycloamine compounds, such as those exhibiting imipramine-like antidepressant activity, which correspond to the formula:

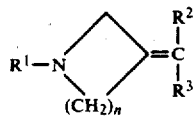

where $R^1$, $R^2$, $R^3$ and n are as previously defined.

A compound corresponding to the above formula can be incorporated as an active therapeutic agent in pharmaceutical compositions. The pharmaceutical compositions are prepared in a form suitable for administering to a living animal.

Pharmaceutical compositions for oral administration are preferably solids and can take the form of capsules, tablets or coated tablets containing carriers conveniently used in the pharmaceutical art. Suitable tableting excipients include lactose, potato and maize starches, talc, gelatin, and stearic and silicic acids, magnesium stearate, and polyvinyl pyrrolidone.

For parenteral administration the carrier or excipient can be a sterile parenterally acceptable liquid (e.g., water), or a parenterally acceptable oil (e.g., arachis oil), contained in ampoules.

In compositions for rectal administration the carrier can comprise a suppository base such as cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage unit forms according to the invention. Each dosage unit adapted for oral administration may conveniently contain 10 to 40 mg of the active ingredient; each dosage unit adapted for intracardial or intravenous administration may conveniently contain 1 to 2 mg per cc of the active ingredient; whereas each dosage unit adapted for intramuscular administration may conveniently contain 5 to 10 mg per cc of the active ingredient. Daily dosages should preferably range from 10 mg to 100 mg. The exact individual dosages as well as daily dosages are determined according to standard medical principles under the direction of a physician or veterinarian.

Antidepressant Activity of Methylene cycloamine Compounds

Antidepressant agents block many of the behavioral and physiological effects of tetrabenazine and reserpine, such as motor depression, hypothermia, and ptosis. Tetrabenazine is chemically related to reserpine which produces depression in humans (Davies, 1964)[1]. Because the onset of action of tetrabenazine is faster than that of reserpine, the former compound is more widely used as a tool for screening potential antidepressant drugs.

[1]Davies, E. D., Depression. Cambridge University Press, New York, 1964.

For the purpose of testing the antidepressant activity of methylene-cycloamine compounds, five adult female mice (ICR-DUB strain) are given 20 mg/kg IP of test compound 30 minutes prior to the administration of a ptotic dose (32 mg/kg IP) of tetrabenazine (as the methane sulfonate salt). Thirty minutes later the presence or absence of complete eyelid closure (ptosis) is assessed in each animal.

For compounds which produced blockage of ptosis in all animals, and $ED_{50}$ value is obtained using a minimum of three geometrically spaced dosages with five mice/dose. Protective $ED_{50}$ values are determined by probit analysis with 95% confidence limits and slope functions calculated by the method of Litchfield and Wilcoxon (1949)[2].

[2]Litchfield, J. T., Jr. and Wilcoxon, F. A simplified method of evaluating dose-effect experiments. J. Pharm. Exp. Ther. 96, 99–113, 1949.

Typical $ED_{50}$ values for reference antidepressant agents are shown in Table 1.

Table 1

| Blockade of Tetrabenazine-Induced Ptosis in Mice | | |
|---|---|---|
| Compound | $ED_{50}$ (95% confidence limits) mg/kg IP | slope |
| imipramine | 0.3 | (0.1–0.6) | 2.6 |
| | 0.4 | (0.2–0.9) | 2.5 |
| | 0.5 | (0.2–1.2) | 2.3 |
| viloxazine | 1.5 | (0.7–3.2) | 2.5 |

In accordance with the above described test and evaluation procedures, 1-isopropyl-3-diphenyleneazetidine oxalate has an $ED_{50}$ mg/kg (IP) of 2.18 (confidence limits, 1.18–4.03), and 1-methyl-3-diphenylmethyleneazetidine has an $ED_{50}$ mg/kg of 1.48 (confidence limits, 0.84–2.5). The antidepressant properties of 3-disubstituted methylene-pyrrolidine compounds are disclosed in U.S. Pat. No. 3,732,247.

the following examples are illustrative of the application of the present invention process for production of methylene-cycloamine compounds, and the synthesis of starting materials suitable for their preparation. The reactants and other specific ingredients are presented as being typical, and various modifications can be devised in view of the foregoing disclosure within the scope of the invention.

EXAMPLE 1

This example illustrates the preparation of 3-chloro-1-methylazetidine hydrochloride.

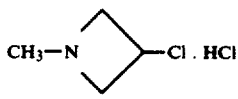

A mixture of dilute sodium hydroxide solution and 700 ml of toluene was used to partition 46 g (0.134 mole) of 3-diphenylmethoxy-1-methylazetidine oxalate. The toluene solution was dried over anhydrous sodium sulfate and further dried by azeotropic distillation of toluene to 300 ml final volume. The dried toluene solution was treated with 10% palladium-on-charcoal and hydrogenated at 45 psi at 80° C. for 5 hours. The mixture was filtered and 41 g (0.264 mole) of carbon tetrachloride was added to the filtrate. After cooling the resulting solution in an ice-methanol bath, 53.5 g (0.145 mole) of trioctylphosphine was added in one portion with stirring. The temperature rose rapidly to a maximum of 50° C. The solution was stirred for 30 minutes and distilled to a pot temperature of 150° C. The distillate was acidified with ethereal hydrogen chloride. The resulting crystals were separated by filtration and dried in vacuo, yielding 8.5 g of product (45%).

A solution of the base, 3-chloro-1-methylazetidine was prepared by partitioning 3-chloro-1-methylazetidine hydrochloride between toluene and dilute sodium hydroxide, drying the toluene solution with anhydrous sodium sulfate and passing the solution through a ½"×21" column of No. 4A molecular sieves.

EXAMPLE 2

This example illustrates the preparation of α,α-diphenyl-α-(1-isopropyl-3-azetidinyl)acetonitrile.

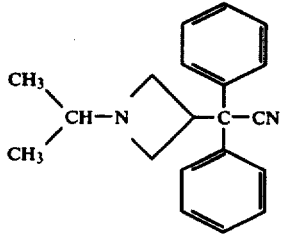

Procedure A

To 250 ml of triethylamine was added 114 g (0.4 mole) of 1-isopropyl-3-azetidinyl mesylate oxalate. About 250 ml of dry toluene was added followed by 77 g of anhydrous magnesium sulfate, and the mixture blended for about one minute and then filtered. The filtrate was added over a period of one hour to a refluxing mixture prepared by refluxing 18.5 g (0.44 mole) of 57% sodium hydride (in mineral oil) and 77.2 g (0.4 mole) of diphenylacetonitrile in 1500 ml of dry toluene for 3 hours. The mixture was refluxed for 2 hours, cooled and extracted with dilute hydrochloric acid. The organic layer was extracted five times with water and all the aqueous layers combined. The aqueous solution was made basic with sodium hydroxide and extracted with chloroform which was dried (sodium sulfate) and concentrated. The residue was crystallized from isooctane, yielding 68 g (58%) of product, m.p. 92°–95° C. Recrystallization from isooctane raised the melting point to 93°–95° C.

Analysis: Calculated for $C_{20}H_{22}N_2$: C,82.72; H,7.64; N,9.65. Found: C,82.72; H,7.73; N,9.55.

Procedure B

A mixture of 40.42 g (0.96 mole) of 57% sodium hydride and 168 g (0.87 mole) of diphenylacetonitrile was refluxed in one liter of dry toluene for 3 hours. In a separate flask 100 g (0.87 mole) of methanesulfonyl chloride was added dropwise at 20° C. to a stirred solution of 100 g (0.87 mole) of 1-isopropyl-3-azetidinol and 101 g (1 mole) of triethylamine in 700 ml dry benzene. The mixture was stirred at 25° C. for 2 hours and filtered. The filter cake was washed with benzene. The combined filtrates were added dropwise over a period of about 30 minutes to the prepared refluxing suspension of the sodium salt of diphenylacetonitrile. After refluxing 1.5 hours, the cooled solution was washed with water and extracted with dilute hydrochloric acid followed by extraction with water. The aqueous extracts were combined, made basic with sodium hydroxide and extracted with chloroform. The chloroform solution was dried (sodium sulfate) and concentrated. The residue was crystallized from isooctane, yielding 142 g (56%) of product.

EXAMPLE 3

This example illustrates the preparation of α,α-diphenyl-α-(1-cyclohexyl-3-azetidinyl)acetonitrile.

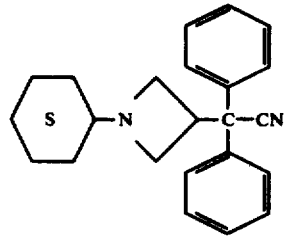

Methylene chloride containing 191 g (1.0 mole) of 1-cyclohexyl-3-azetidinol hydrochloride was extracted with dilute aqueous sodium hydroxide solution and the organic layer separated, dried over sodium sulfate, filtered and concentrated in vacuo. The residue was dissolved in dry benzene and mixed by stirring with 116 g (1.05 mole) of triethylamine and thereafter cooled with an ice bath. To the cold stirred solution was added dropwise 115 g of methanesulfonyl chloride and stirring was continued at room temperature for three hours and the mixture thereafter filtered. To one liter of dry toluene containing 50.0 g (1.0 mole) of sodium hydride at 45°–50° C. was added 193 g (1 mole) of diphenylacetonitrile and the mixture refluxed with stirring for two hours. To this solution the foregoing filtrate was added at a fast dropwise rate. After addition was complete, reflux was continued for two hours and thereafter the solution was stirred overnight. An equivalent volume of isooctane was added and the solution extracted four times with dilute hydrochloric acid solution. The acid layers obtained in each extraction was combined, made basic with a mixture of 50% sodium hydroxide and ice and extracted with chloroform. The chloroform layer was dried, filtered and concentrated in vacuo. The residue was crystallized by adding isopropyl ether and thereafter the solid recrystallized from isopropyl ether to yield 58.0 g (18%) of product melting at 111°–114° C.

Analysis: Calculated for $C_{23}H_{26}N_2$: C,83.59; H,7.93; N,8.48. Found: C,83.24; H,7.94; N,8.27.

Following the same procedure, employing 1-ethyl-3-azetidinol hydrochloride instead of 1-cyclohexyl-3-azetidinol hydrochloride yields α,α-diphenyl-α-(1-ethyl-3-azetidinyl)acetonitrile.

EXAMPLE 4

This example illustrates the preparation of α,α-diphenyl-α-(1-methyl-3-azetidinyl)acetamide hydrochloride starting material.

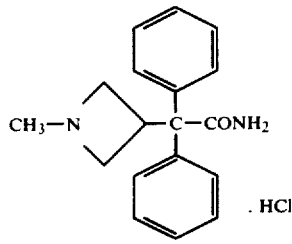

To 60 ml of concentrated sulfuric acid preheated to 60° C. was added 21.7 g (0.082 mole) of α,α-diphenyl-α-(1-methyl-3-azetidinyl)acetonitrile at a rate so as to maintain a temperature of 60°–70° C. The solution obtained was heated to 70° C. for 18 hours and extracted with chloroform. The chloroform extract was dried over sodium sulfate and concentrated and the residue crystallized from ethyl acetate-isopropyl alcohol to give 13.8 g of the free base (60%) melting at 171°–174° C. The base was treated with hydrogen chloride in isobutyl methyl ketone and the salt recrystallized from isopropyl alcohol, yielding 9 g of product melting at 182°–185° C.

Analysis: Calculated for $C_{18}H_{21}ClN_2O$: C,68.24; H,6.68; N,8.84. Found: C,67.88; H,6.72; N,8.78.

EXAMPLE 5

This example illustrates the preparation of α,α-diphenyl-α-(1-isopropyl-3-azetidinyl)acetamide starting material.

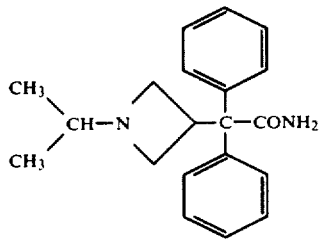

To 80 ml of concentrated sulfuric acid preheated to 70° C. was added 25 g (0.86 mole) of α,α-diphenyl-α-(1-isopropyl-3-azetidinyl)acetonitrile at a rate to maintain a temperature of 65°–75° C. The solution was heated at 70° C. for 18 hours and poured on ice. The mixture was made basic with 50% sodium hydroxide (while cooling with ice) and extracted with chloroform. The chloroform was dried (sodium sulfate) and concentrated. The residue was crystallized from ethyl acetate-ethanol to yield 15.7 g (59%) of product melting at 181°–184° C.

Analysis: Calculated for $C_{20}H_{24}N_2O_1$: C,77.89; H,7.84; N,9.08. Found: C,77.89; H,7.88; N,8.98.

Following the same procedure, employing α,α-diphenyl-α-(1-ethyl-3-azetidinyl)acetonitrile instead of the 1-isopropyl derivative yields α,α-diphenyl-α-(1-ethyl-3-azetidinyl)acetamide.

EXAMPLE 6

This example illustrates the preparation of α,α-diphenyl-α-[1-(1-phenylethyl)-3-azetidinyl]acetamide starting material.

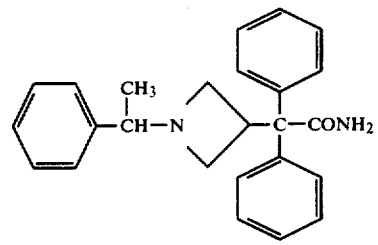

To 100 ml of concentrated sulfuric acid preheated to 70° C. was added with stirring, 50 g (0.142 moles) of α,α-diphenyl-α-[1-(1-phenylethyl)-3-azetidinyl]acetonitrile at a rate to maintain a temperature of 65°–70° C. The solution was heated at 72°–75° C. for 18 hours. The acid solution was poured onto ice and thereafter made basic with 50% aqueous sodium hydroxide solution and extracted with chloroform. The chloroform extract was dried over anhydrous sodium sulfate and concentrated by distillation. The residue was crystallized from isopropyl ether to give 28.5 g (54%) of materials melting at 152°–153.5° C. A sample was recrystallized from isopropyl ether-isopropyl alcohol, yielding a product melting at 153°–154° C.

Analysis: Calculated for $C_{25}H_{26}N_2O$: C,81.05; H,7.07; N,7.56. Found: C,80.83; H,7.07; N,7.40.

Following the same procedure, employing α,α-diphenyl-α-(1-cyclohexyl-3-azetidinyl)acetonitrile instead of the 1-phenylethyl derivative yields α,α-diphenyl-α-(1-cyclohexyl-3-azetidinyl)acetamide.

EXAMPLE 7

This example illustrates the preparation of α,α-diphenyl-α-(1-ethyl-3-pyrrolidinyl)acetamide starting material.

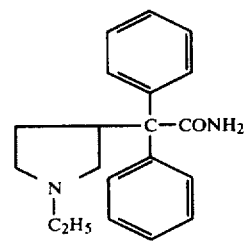

To 240 ml of concentrated sulfuric acid was added 60 g (0.21 mole) of α,α-diphenyl-α-(1-ethyl-3-pyrrolidinylacetonitrile. The mixture was shaken until solution took place and allowed to stand at 70° C. for 24 hours. The solution was poured on ice, made basic with ammonium hydroxide and extracted with about 1000 ml of ethyl acetate. The ethyl acetate solution was dried with anhydrous sodium sulfate and concentrated to about 200 ml. The white crystals that were obtained on cooling were recrystallized from an ethyl acetate-ligroin mixture, yielding 34 g (52.5%); m.p. 141°–142° C.

Analysis: Calculated for $C_{20}H_{24}N_2O$: C,77.88; H,7.84; N,9.09. Found: C,79.70; H,8.18; N 8.83.

EXAMPLE 8

This example illustrates the preparation of α-(1-cyclohexyl-3-pyrrolidinyl)-α,α-diphenylacetamide starting material.

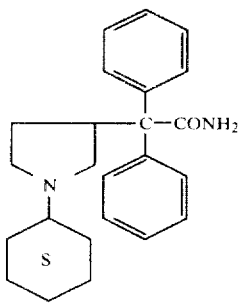

To 80 ml of concentrated sulfuric acid was added 20 g (0.057 mole) of α-(cyclohexyl-3-pyrrolidinyl)-α,α-diphenylacetonitrile. The mixture was shaken until solution occurred while being cooled in an ice bath until heat was no longer evolved. The solution was heated at 70° C. for 48 hours, poured on ice and made basic with ammonium hydroxide. The resulting white solid precipitate was taken up in ethyl acetate and the solution dried over sodium sulfate. The solution was concentrated and the residual oil taken up in hot ligroin, filtered and allowed to stand overnight at room temperature. The resulting crystals were recrystallized from ligroin, yielding 9.0 g (42.5%); m.p. 119°–121° C.

Analysis: Calculated for $C_{24}H_{30}N_2O$: C,79.51; H,8.34; N,7.73. Found: C,79.69; H,8.51; N,7.58.

EXAMPLE 9

This example illustrates the preparation of 1-methyl-3-diphenylmethyleneazetidine.

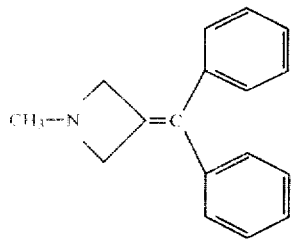

To 150 ml of methanol was added 4.6 (0.20 mole) of sodium pellets, and upon dissolution, 14.0 g (0.05 mole of α,α-diphenyl-α-(1-methyl-3-azetidinyl)acetamide was added. To this stirring suspension was added, dropwise, 16.0 g (0.10 mole) of liquid bromine, maintaining room temperature with ice-bath cooling. Stirring was continued for two hours. The solution was concentrated in vacuo, and the residue was treated with 100 ml of 6 N sulfuric acid, and refluxed for 18 hours. The acid mixture was made basic with sodium hydroxide and extracted with chloroform. The chloroform layer was dried, filtered, and concentrated in vacuo.

The residue was dissolved in isopropanol and treated with maleic acid, and the salt was recrystallized in isopropanol. The salt was partitioned between isopropyl ether and dilute sodium hydroxide. The ether was dried, filtered, and concentrated in vacuo. The residue was crystallized from isooctane, yielding 7.0 g; m.p. 93°–95° C.

Analysis: Calculated for $C_{17}Hahd 17N$: C, 86.76; H, 7.28; N, 5.95. Found: C, 86.74; H, 7.34; N, 5.81.

Following the same procedure, employing the 1-ethyl derivatives or the 1-cyclohexyl derivative in place of the 1-methyl derivative, yields 1-ethyl-3-diphenylmethyleneazetidine and 1-cyclohexyl-3-diphenylmethyleneazetidine, respectively.

EXAMPLE 10

This example illustrates the preparation of 1-isopropyl-3-diphenylmethyleneazetidine oxalate.

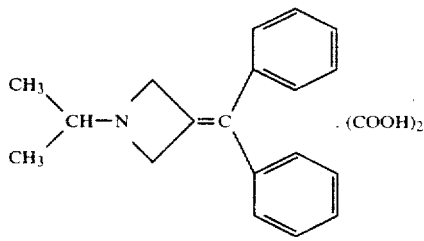

To 125 ml of methanol was added 18.1 g (0.336 mole) of sodium methoxide and 26 g (0.084 mole) of α,α-diphenyl-α-(1-isopropyl-3-azetidinyl)acetamide. To the stirred mixture was added dropwise 26.8 g (0.168 mole) of bromine over a period of 30 minutes, and the resulting solution was brought to reflux for 2 hours and concentrated. The residue was dissolved in 6 N sulfuric acid and brought to reflux for 24 hours and extracted with isopropyl ether. The acid layer was made basic with sodium hydroxide and extracted with chloroform. The chloroform was dried ($Na_2SO_4$) and concentrated. The residue was treated with 0.08 mole of oxalic acid in ethanol. The resulting crystals were recrystallized three times from ethanol, yield 3 g (10%); m.p. 204°–205° C.

Analysis: Calculated for $C_{21}H_{23}N_1O_4$: C,71.35; H,6.56; N,3.96. Found: C,70.95; H,6.53; N,3.90.

Following the same procedure up to the addition of oxalic acid, employing the 1-phenyl-ethyl derivative or the 1-(1-phenylethyl) derivative instead of the 1-isopropyl derivative yields 1-phenylethyl-3-diphenylmethyleneazetidine and 1-(1-phenylethyl)-3-diphenylmethyleneazetidine.

EXAMPLE 11

This example illustrates the preparation of 1-methyl-3-diphenylmethylenepyrrolidine.

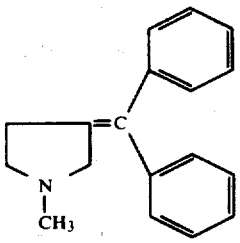

To a solution of 59.5 g (1.1 mole) of sodium methoxide in 850 ml of methanol was added 81 g (0.276 mole) of α,α-diphenyl-α-(1-methyl-3-pyrrolidinyl)acetamide. To this stirred solution was added dropwise 90 g (0.56 mole) of bromine in 150 ml of methanol and the solution brought to reflux for 1.5 hours. The solution was concentrated in vacuo and the residue partitioned between chloroform and water. The chloroform was concentrated and the residue dissolved in 600 ml of 6 N sulfuric acid which was heated to 100° C. for 2.5 hours. The solution was made basic sodium hydroxide and extracted with ethyl acetate. The extract was concentrated and distilled. Yield 42 g; b.p. 150°-160° C./0.2 mm. A portion was crystallized several times from isooctane; m.p. 73°-74° C.

Analysis: Calculated for $C_{18}H_{19}N$: C,86.70; H,7.68; N,5.62. Found: C,86.77; H,7.62; N,5.60.

Following the same procedure, employing α,α-diphenyl-α-(1-ethyl-3-piperidinyl)acetamide or α,α-diphenyl-α-(1-ethyl-4-azepinyl)acetamide as the starting material yields 1-ethyl-3-diphenylmethylenepyrrolidine or 1-ethyl-4-diphenylmethyleneazepine, respectively.

EXAMPLE 12

This example illustrates the preparation of α,α-diphenyl-α-(1-methyl-3-azetidinyl)acetonitrile starting material.

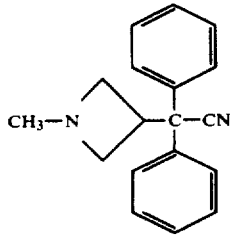

Procedure A

To 4 g (0.11 mole) sodium amide in 300 ml toluene was added 21 g (0.11 mole) of diphenylacetonitrile and the stirred mixture was refluxed in a nitrogen atmosphere for 4 hours. The heat was removed and a solution of 3-chloro-1-methylazetidine was added at a rate to maintain reflux. The solution was refluxed 4 hours, allowed to stand overnight, washed with water and extracted with dilute hydrochloric acid. The aqueous acid layer was made basic with dilute sodium hydroxide and extracted twice with isopropyl ether. The solution was dried (sodium sulfate) and concentrated. The residue was recrystallized from ligroin to yield 6.7 g (27%) of product, m.p. 113°-115° C.

Analysis: Calculated for $C_{18}H_{18}N_2$: C,82.41; H,6.92; N,10.68. Found: C,82.31; H,6.98; N,10.51.

Procedure B

To 800 ml of ethanol was added 59 g (0.13 mole) of α,α-diphenyl-α-[1(1-phenylethyl)-3-azetidinyl]acetonitrile methobromide, 7.12 g (0.013 mole) of potassium hydroxide, and 0.25 g 10% palladium-on-charcoal. The mixture was shaken in a Parr hydrogenation apparatus at room temperature under an initial pressure of 45 psi of hydrogen for 24 hours. The mixture was filtered and the filtrate concentrated in vacuo. The residue was crystallized from isooctane. The yield of product was 21.7 g (64%), melting at 112°-115° C.

What is claimed is:

1. A process for preparing methylene-cycloamine derivatives which comprises the steps of (1) reacting a substituted acetamide compound with bromine and alkali metal alkoxide to produce a carbamate intermediate, wherein said substituted acetamide starting material corresponds to the formula:

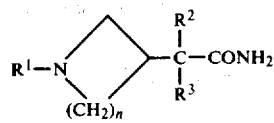

wherein $R^1$ is selected from lower-alkyl, phenyl-lower-alkyl and cycloalkyl radicals, $R^2$ and $R^3$ are selected from phenyl and lower-alkylphenyl radicals, and n is an integer between 1 and 4; and (2) heating said carbamate intermediate in an acidic medium to yield a methylene-cycloamine product corresponding to the formula:

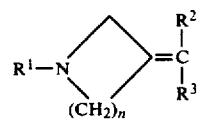

wherein $R^1$, $R^2$, $R^3$ and n are as previously defined.

2. A process in accordance with claim 1 wherein the alkali metal alkoxide in step (1) is sodium or potassium methoxide.

3. A process in accordance with claim 1 wherein the reaction temperature in step (1) is maintained in the range between about 0° C. and 50° C.

4. A process in accordance with claim 1 wherein the reaction temperature in step (2) is maintained in the range between about 75° C. and 200° C.

5. A process in accordance with claim 1 wherein the acid strength of the acidic medium in step (2) is at least 1 normal.

6. A process in accordance with claim 1 wherein n is the integer 1 or 2.

7. A process in accordance with claim 1 wherein the methylene-cycloamine product is 1-isopropyl-3-diphenylmethyleneazetidine.

8. A process in accordance with claim 1 wherein the methylene-cycloamine product is 1-ethyl-3-diphenylmethylenepyrrolidine.

9. A process in accordance with claim 1 wherein the methylene-cycloamine product is 1-methyl-3-diphenylmethyleneazetidine.

10. A process for preparing methylene-cycloamine derivatives corresponding to the formula:

wherein R¹ is selected from lower-alkyl, phenyl-lower-alkyl and cycloalkyl radicals, R² and R³ are selected from phenyl and lower-alkylphenyl radicals, and n is an integer between 1 and 4; said process comprising the step of heating in an acidic medium a carbamate compound corresponding to the formula:

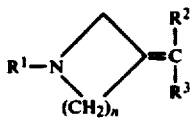

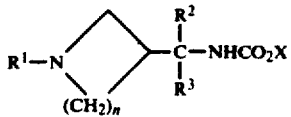

where R¹, R², R³ and n are as previously defined, and X is an alkyl radical containing between one and eight carbon atoms.

11. A process in accordance with claim 10 wherein the carbamate compound is heated in an aqueous medium at a temperature between about 75° C. and 200° C.

12. A process in accordance with claim 10 wherein the acidic medium has an acid strength of at least 1 normal provided by a mineral acid.

13. A process in accordance with claim 10 wherein the methylene-cycloamine product is 1-isopropyl-3-diphenylmethyleneazetidine.

14. A process in accordance with claim 10 wherein the methylene-cycloamine product is 1-methyl-3-diphenylmethyleneazetidine.

15. A process in accordance with claim 10 wherein the methylene-cycloamine product is 1-ethyl-3-diphenylmethylenepyrrolidine.

* * * * *